US00PP29946P2

(12) United States Plant Patent
Van Swieten

(10) Patent No.: US PP29,946 P2
(45) Date of Patent: Dec. 4, 2018

(54) ***PHALAENOPSIS* ORCHID PLANT NAMED 'PHALFUCAL'**

(50) Latin Name: ***Phalaenopsis* hybrid**
Varietal Denomination: PHALFUCAL

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/731,848

(22) Filed: Aug. 14, 2017

(51) Int. Cl.
*A01H 5/02* (2018.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new and distinct variety of *Phalaenopsis* plant named 'PHALFUCAL', particularly characterized by having dark red-purple flowers with a small light purple edge and center, 1 to 3 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALFUCAL'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFUCAL'.

The new *Phalaenopsis* plant is a product of a planned breeding program conducted by the inventor in Bleiswijk, The Netherlands. The objective of this breeding program was to create a new *Phalaenopsis* plant with numerous attractive and unique dark red-purple flowers with a small light purple edge and center, suitable for potted plant production.

The new *Phalaenopsis* plant 'PHALFUCAL' is a result of cross-pollination made by the inventor in March 2008 in Bleiswijk, The Netherlands of the proprietary female, or seed parent, *Phalaenopsis* hybrid '6240-02' (unpatented) with the proprietary male, or pollen parent, *Phalaenopsis* hybrid '01-1806' (unpatented).

The new *Phalaenopsis* was selected by the inventor as a single plant within the progeny of the stated cross-pollination in a controlled greenhouse in Bleiswijk, The Netherlands in February 2011. Asexual reproduction of the new *Phalaenopsis* plant by meristem tissue culture since 2014 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 25, 2017. 'PHALFUCAL' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFUCAL' as a new and distinct variety of *Phalaenopsis* plant.

1) Dark red-purple flowers with a small light purple edge and center;
2) 1 to 3 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in May 2017. Colors in the photographs may differ from the color values cited in the detailed botanical description, which accurately describe the actual colors of the new variety.

DESCRIPTION OF THE NEW VARIETY

Figure 1:
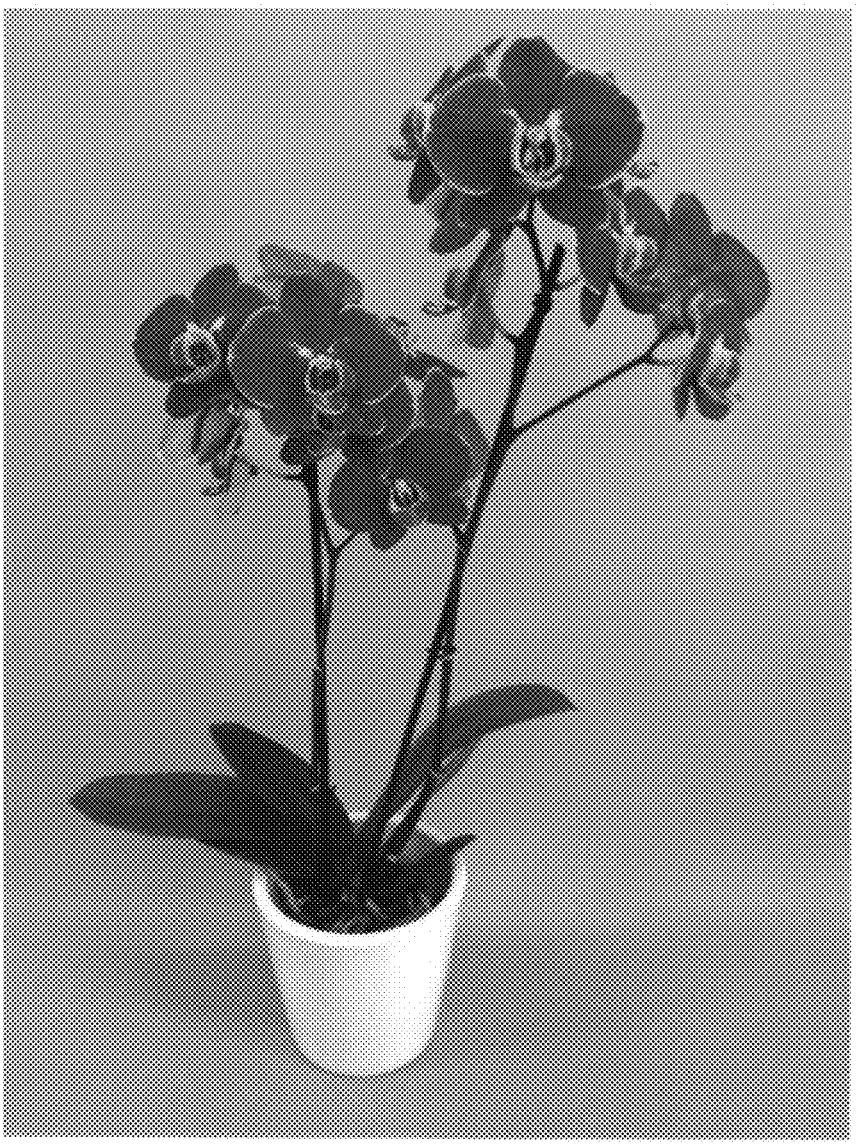
FIG. 1 shows the overall plant habit, including blooms and foliage of 'PHALFUCAL'.
Figure 2:
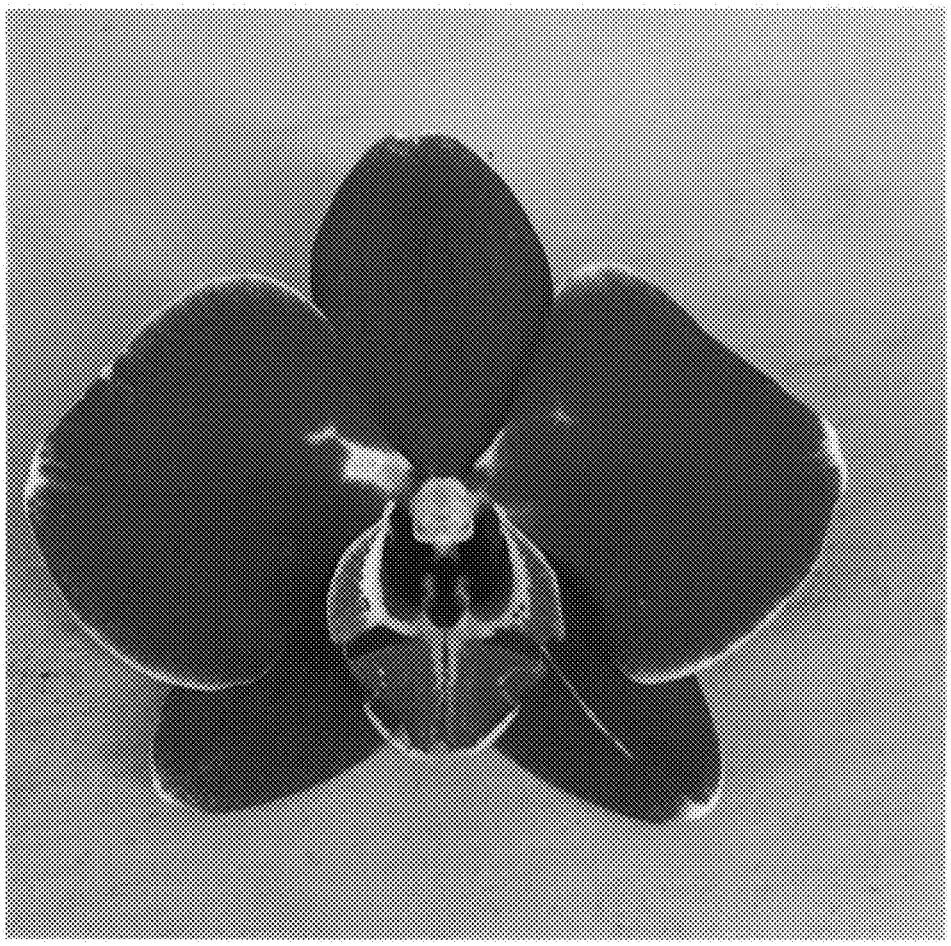
FIG. 2 shows a close-up of a flower of 'PHALFUCAL'.
Figure 3:
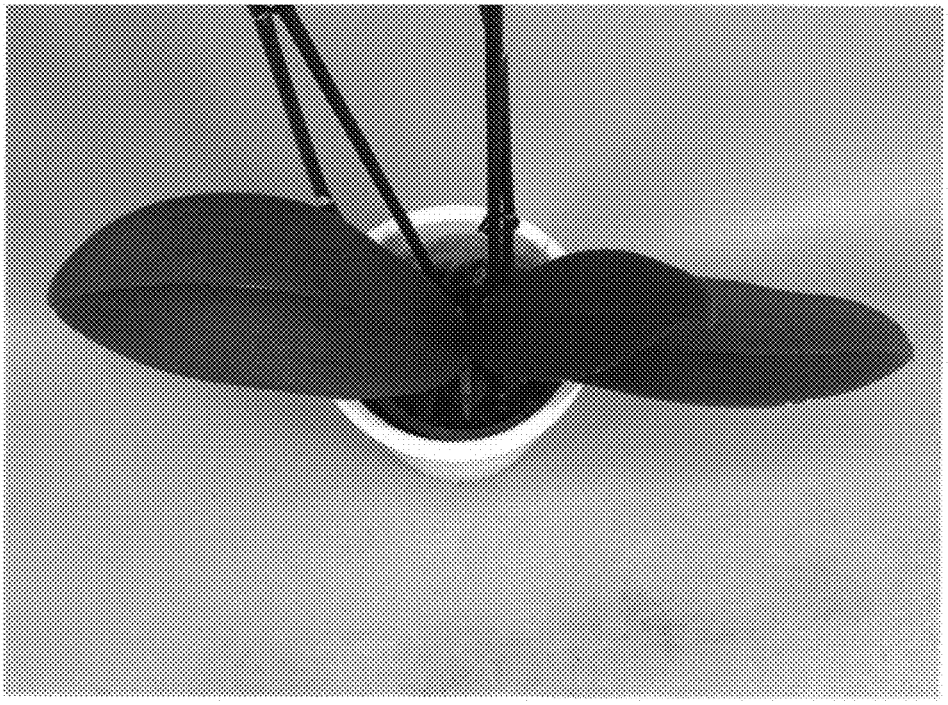
FIG. 3 shows a close-up of the leaves of 'PHALFUCAL'.

The following detailed description sets forth the distinctive characteristics of 'PHALFUCAL'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in May 2017 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFUCAL'.

Parentage:

*Female parent*.—*Phalaenopsis* cultivar '6240-02' (unpatented).

*Male parent*.—*Phalaenopsis* cultivar '01-1806' (unpatented).

Propagation:

*Type*.—Meristem tissue culture.

Roots:

*Root description*.—Greyed-green colored roots (RHS 190B/C) with branching lateral roots having slightly red-purple colored root tips (RHS N77B).

Plant:

*Commercial crop time to flowering*.—Approximately 48 to 50 weeks from a rooted cutting to finish in a 12 cm pot.

*Growth habit of peduncle*.—Standard, green leaves, raceme to panicle.

*Height* (*from soil level to top of inflorescence*).—Approximately 46.0 cm to 56.0 cm.

*Width* (*measured from leaf tips*).—About 37.0 cm to 39.0 cm.

*Vigor*.—Moderate.

Leaves:

*Mature leaves*.—Quantity per plant: 6 to 8 leaves are produced before flowering. Length (fully expanded): 19.0 cm to 21.0 cm. Width: 7.5 cm to 8.5 cm. Shape: Oblong. Base shape: Moderately elongated. Apex: Obtuse unequal. Leaf blade angle with the petiole (measured from the horizontal position): Between 20 degrees and 35 degrees. Leaf margin: Entire. Color: Upper surface: RHS 146A. Lower surface: RHS 146B with diluting purple edge (RHS N77A). Texture: Rough. Thickness: 2.3 mm to 2.6 mm. Venation: Pattern: Parallel. Color of the midvein: Upper surface: RHS 147A. Lower surface: RHS 146A.

Peduncle:

*Quantity per plant*.—1 to 3.

*Number of flowers per peduncle*.—8 to 13.

*Length*.—46.0 cm to 56.0 cm.

*Diameter*.—6.4 mm to 6.6 mm.

*Strength*.—Moderate.

*Aspect*.—Upright to slightly pendant.

*Texture*.—Smooth.

*Color*.—Mix of brown (RHS N200A) and green (RHS 146C).

*Internode length*.—7.0 cm to 8.0 cm.

*Callosities*.—None.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 220.0 mm to 250.0 mm.

*Flowering time*.—First flowers can be expected 10 to 11 months after planting in a 12 cm (diameter) pot.

*Flower*.—Height: 80.0 mm to 82.0 mm. Diameter: 85.0 mm to 90.0 mm. Depth of lip: 22.0 mm to 24.0 mm.

*Flower longevity*.—On the plant: 13 to 18 weeks.

*Fragrance*.—Absent.

*Flower bud*.—Average size: Medium. Length: 18.0 mm to 20.0 mm. Width: 16.0 mm to 18.0 mm. Shape: Egg shaped. Color: Diluting red-purple (RHS N79C) and green (RHS 146D).

*Petals*.—Arrangement: Open/free. Shape: Semi-circular. Apex: Emarginated asymmetric. Margin: Slightly undulated. Length (from base to tip): 40.0 mm to 42.0 mm. Width: 47.0 mm to 49.0 mm. Color (when fully opened): Upper surface: Basic color: Dark red-purple (RHS N79C). Over color: Small light purple edge (RHS 76D) and light purple center (RHS 76C). Lower surface: Basic color: Light purple (RHS 76C). Over color: Light purple (RHS N78D) at the base.

*Dorsal sepal*.—Shape: Elliptic. Apex: Emarginated symmetric. Margin: Entire. Length (from base to tip): 42.0 mm to 44.0 mm. Width: 27.0 mm to 29.0 mm. Color (when fully opened): Upper surface: Basic color: Dark red-purple (RHS N79C). Over color: Slightly light purple (RHS 76C) at the apex. Lower surface: Basic color: Light purple (RHS 76C). Over color: Light purple (RHS N78D).

*Lateral sepals*.—Shape: Ovate. Apex: Obtuse asymmetric. Margin: Entire. Length (from base to tip): 43.0 mm to 45.0 mm. Width: 24.0 mm to 26.0 mm. Color (when fully opened): Upper surface: Basic color: Dark red-purple (RHS N79C). Over color: Slightly light purple (RHS 76C) at the apex. Lower surface: Basic color: Light purple (RHS 76C). Over color: Light purple (RHS N78D) vein in the middle.

*Labellum* (*lip*).—Whiskers: Present. Length of whiskers: 19.0 mm to 21.0 mm. Color of whiskers: White (RHS NN155C) with purple dots (RHS N79C) at the base and dark red dots (RHS 187B) toward the tip. Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Slightly undulated. Length: 18.0 mm to 20.0 mm. Width: 14.0 mm to 16.0 mm. Color: White (RHS NN155C) with dark red region (RHS 187B) at the base and purple stripes (RHS N78B) at the edge; slightly yellow (RHS 6B) toward one margin.

*Apical lobe*.—Shape: Triangular. Margin: Entire. Length: 20.0 mm to 22.0 mm. Width: 21.0 mm to 23.0 mm. Color: Yellow at the base (RHS 6B) with dark red wings (RHS 60B) and dark red spots (RHS 187B) in the middle; purple (RHS N78B) toward whiskers.

*Callus*.—Average size: Medium. Height: 5.0 mm to 6.0 mm. Length: 5.0 mm to 6.0 mm. Width: 4.0 mm to 5.0 mm. Color: Yellow (RHS 12A) and dark red (RHS 187A) in the middle.

Reproductive organs:

*Column*.—Length: 8.0 mm to 10.0 mm. Diameter: 5.8 mm to 6.1 mm. Color: White (RHS NN155C) at the base; light purple (RHS N78D).

*Pollinia*.—Quantity: 2. Diameter: 1.0 mm to 1.2 mm. Color: Orange (RHS 24A).

*Ovary*.—Length: 7.0 mm to 9.0 mm. Diameter: 2.1 mm to 2.3 mm.

*Pedicel*.—Length: 34.0 mm to 36.0 mm. Diameter: 2.5 mm to 2.7 mm. Color: Green (RHS 145C) dotted (diluting RHS N77D) at the base; light purple (RHS 76C) toward the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

COMPARISON WITH PARENTAL LINES AND MOST SIMILAR VARIETIES

'PHALFUCAL' differs from female parent plant '6240-02' (unpatented) in that 'PHALFUCAL' has dark red-purple flowers, an emarginated dorsal sepal apex and white whiskers with purple dots at the base and dark red dots toward the tip, whereas '6240-02' has light purple flowers, an obtuse dorsal sepal apex and evenly colored purple whiskers.

'PHALFUCAL' differs from male parent plant '01-1806' (unpatented) in that 'PHALFUCAL' has an emarginated dorsal sepal apex and white whiskers with purple dots at the base and dark red dots toward the tip, whereas '01-1806' has a slightly emarginated dorsal sepal apex and red-purple whiskers with white edge.

'PHALFUCAL' is most similar to the commercial *Phalaenopsis* plants named 'PHALFENCK' (U.S. Plant Pat. No. 27,460) and 'PHALFUNWUQ' (unpatented). 'PHALFUCAL' differs from the commercial variety 'PHALFENCK' in that 'PHALFUCAL' has dark red-purple flowers and a yellow callus with dark red in the middle, whereas 'PHALFENCK' has dark red flowers and a dark red callus. Additionally, 'PHALFUCAL' has larger flowers and longer whiskers than 'PHALFENCK'.

'PHALFUCAL' differs from the commercial variety 'PHALFUNWUQ' in that 'PHALFUCAL' has dark red-purple flowers and a yellow callus with dark red in the middle, whereas 'PHALFUNWUQ' has dark red flowers and a dark red callus with light yellow on the sides and darker yellow tips. Additionally, 'PHALFUCAL' has larger flowers and slightly longer whiskers than 'PHALFUNWUQ'.

I claim:

1. A new and distinct variety of *Phalaenopsis* plant named 'PHALFUCAL', substantially as described and illustrated herein.

* * * * *